United States Patent [19]

Shigenobu et al.

[11] Patent Number: 5,766,870
[45] Date of Patent: Jun. 16, 1998

[54] METHOD OF QUANTITATIVE DETERMINATION OF SODIUM IONS

[75] Inventors: Kayoko Shigenobu, Mishima; Norihito Aoyama, Shizuoka, both of Japan

[73] Assignee: Kyowa Medex Co., Ltd., Tokyo, Japan

[21] Appl. No.: 601,031

[22] PCT Filed: Aug. 22, 1994

[86] PCT No.: PCT/JP94/01384

§ 371 Date: May 3, 1996

§ 102(e) Date: May 3, 1996

[87] PCT Pub. No.: WO95/06135

PCT Pub. Date: Mar. 2, 1995

[30] Foreign Application Priority Data

Aug. 23, 1993 [JP] Japan ................... 5-207834

[51] Int. Cl.$^6$ .............................. C12Q 1/34; G01N 33/53
[52] U.S. Cl. ................................. 435/18; 435/962
[58] Field of Search .................... 435/18, 4, 7.7, 435/7.72, 22, 25, 962

[56] References Cited

U.S. PATENT DOCUMENTS 5,384,247 1/1995 Berry et al. .......................... 435/22

FOREIGN PATENT DOCUMENTS

WO 00275 4/1988 European Pat. Off. .
0309525 10/1988 European Pat. Off. .

OTHER PUBLICATIONS

Hill, J. Effects of Various Concentrations of Na+ and Mg+2 on the Activity of Beta–Galactosidase. Biochimica et Biophysica Acta 250 530–537, 1971.
Berry et al., "Enzymatic Determination of Sodium in Serum," Clin. Chem. 1988, 34, 2295–2298, 1988.
Clinical Chemistry, vol. 34, No. 11 (1988) 2295–2298.

*Primary Examiner*—Ralph Gitomer
*Attorney, Agent, or Firm*—Fitzpatrick, Cella, Harper & Scinto

[57] ABSTRACT

The present invention relates to a method of quantitative determination of sodium ions in a sample using β-galactosidase, wherein the β-galactosidase reaction is conducted in the presence of at least one chelating agent selected from of 1,2-cyclohexanediamine-N,N,N',N'-tetraacetic acid, ethylenediamine-tetraacetic acid, triethylenetetranine-hexaacetic acid, diethylenetriamine-N,N',N'',N''-pentaacetic acid, 1,3-diminopropan-2-ol-N,N',N'-tetraacetic acid, ethylenediamine-N,N'-dipropionic acid dihydrochloride, ethylenediamine-tetrakis (methylenesulfonic acid), iminodiacetic acid, hydroxyimino-diacetic acid and nitrilotriacetic acid.

The method of quantitative determination of sodium ions of the present invention is useful in clinical examinations and the accuracy in the measurement by the method is high.

4 Claims, 1 Drawing Sheet

METHOD OF QUANTITATIVE DETERMINATION OF SODIUM IONS

TECHNICAL FIELD

The present invention relates to a method of quantitative determination of sodium ions using a chelating agent such as ethylenediamine-tetraacetic acid or the like, which is applicable to clinical examinations.

BACKGROUND ART

There is known a method of quantitative determination of sodium ions existing in a sample collected from a living organism by using the β-galactosidase reaction, the method causes the increase in the activity of the enzyme in proportion to the amount of the sodium ions existing in the sample in which from 0.2 to 5 mM of Cryptofix 221 (trade name) is added to the reaction system in order to prevent the saturation of the enzymatic reaction due to excess sodium ions [see Clinical Chemistry, Vol. 34, p. 2295, 1988]. The use of lithium ions or a small amount, from 0 to 20 mM of a lithium salt of ethylene glycol bis(β-aminoethyl ether)-N, N,N',N'-tetraacetic acid (EGTA) in the quantitative determination method using the β-galactosidase reaction in place of Cryptofix 221 has been disclosed [see Japanese Patent Laid-Open No. 1-503596 (WO88/08127)].

Conventional binding reagents, cryptand, crown ether, etc., which have heretofore been used in the method of quantitative determination of sodium ions using β-galactosidase, are expensive, and it is said that such binding reagents detract from the stability of β-galactosidase. In addition, since the reaction speed of cryptand with sodium ions is low, the reaction system using cryptand takes a long period of time until it reaches a stationary state and therefore rapid measurement is difficult. For these reasons, it is said that the accuracy in the quantitative determination of sodium ions by the use of cryptand is low.

Moreover, regarding the method of using such known binding reagents and lithium ions, the range of the concentration of sodium ions that can be quantitatively determined by the method is narrow and the linearity of the calibration curves in the method is extremely bad. Therefore, the method needs a particular calculable assay device.

DISCLOSURE OF THE INVENTION

In general, it is known that if a large amount of a chelating agent such as ethylenediamine-tetraacetic acid or the like exists in enzymatic reaction, the chelating agent interferes with the enzymatic reaction and it lowers the stability of the enzyme used and lowers the reproducibility of determined values, and it has heretofore been said that the addition of a large amount of a chelating agent to the quantitative determination method using enzymatic reaction lowers the determination accuracy. Contrary to the prior art knowledge, we, the present inventors have found that even when a large amount of a chelating agent is present in the enzymatic reaction using β-galactosidase, the chelating agent does neither interfere with the enzymatic reaction nor lower the stability of the enzyme used but the linearity of the calibration curves in the method is improved and the accuracy in the quantitative determination by the method is improved. On the basis of these findings, we have completed the present invention.

Specifically, the present invention provides a method of quantitative determination of sodium ions in a sample using β-galactosidase, in which the β-galactosidase reaction is conducted in the presence of a particular chelating agent.

The chelating agent for use in the present invention indicates at least one chelating agent selected from 1,2-cyclohexanediamine-N,N,N',N'-tetraacetic acid (CyDTA), ethylenediamine-tetraacetic acid (EDTA), triethylenetetramine-hexaacetic acid (TTHA), diethylenetriamine-N,N,N',N'',N''-penteacetic acid (DTPA), 1,3-diaminopropan-2-ol-N,N,N',N'-tetraacetic acid (DPTA-OH), ethylenediamine-N,N'-dipropionic acid dihydrochloride (EDDP), ethylenediamine-tetrakis(methylenesulfonic acid) [EDTPO], imino-diacetic acid (IDA), hydroxyimino-diacetic acid (HIDA), nitrilo-triacetic acid (NTP) and combinations of these. In general, the chelating agent is employed at a concentration of from 1 to 500 mM. More preferably, CyDTA is used at from 2 to 400 mM, EDTA is at from 25 to 400 mM, TTHA is at from 25 to 400 mM, and DTPA is at from 10 to 400 mM.

The sample containing sodium ions may be any sample that is miscible with aqueous media. According to the method of the present invention, it is possible to measure even the concentration of sodium ions existing in samples as collected from living organisms, such as whole blood, cells, etc., which are difficult to measure by atomic photo-absorptiometry, flame photometry or the like.

The method of quantitative determination of sodium ions using β-galactosidase according to the present invention is such that β-galactosidase is reacted with the substrate for β-galactosidase in a solid phase or a liquid phase, preferably in an aqueous medium, the amount of the substrate that has decreased in the reaction liquid or the amount of the product from the β-galactosidase reaction that has increased in the reaction liquid is measured to thereby determine the β-galactosidase activity in the reaction system, and the amount of the sodium ions corresponding to the activity is calculated.

The aqueous medium indicates an aqueous liquid containing a buffer, a physiological saline, etc. The buffer includes tris(hydroxymethyl) aminomethane-hydrochloride buffers, phosphate buffers, acetate buffers, succinate buffers, oxalate buffers, phthalate buffers, borate buffers, glycine buffers, barbital buffers, Good buffers, etc.

β-galactosidase as referred to herein may be any enzyme that belongs to the enzyme number [EC. 3.2.1.233] and includes β-galactosidases to be collected from animals, microorganisms and vegetables as well as recombinant β-galactosidases to be obtained by modifying such natural β-galactosidases by bioengineering techniques.

The substrate for β-galactosidase may be either a synthetic one or a natural one and includes, for example, β-D-galactoside, aryl-β-D-galactosides, alkyl-β-D-galactosides, 3,6-dihydroxyfluoran-β-D-galactoside, nitrophenyl-β-D-pyranoglycoside, nitrophenyl-β-D-galacoside, 2-nitrophenyl-β-galactopyranoside, lactinol, lactose, 4-methylumbelliferyl-β-D-galactoside, etc. As the activating agent for β-galactosidase, employable is magnesium sulfate, magnesium chloride, magnesium nitrate or the like.

The variation in the amount of the substrate for β-galactosidase that has decreased in the reaction liquid can be obtained, for example, by measuring the decrease in the amount of the substrate, such as the above-mentioned nitrophenyl ester or the like, by means of photo-absorptiometry or the like.

The amount of the β-galactosidase reaction product as formed in the reaction liquid can be obtained, for example, by measuring the amount of the galactose, aglycone, 3,6-dihydroxyfluoran, nitrophenol or the like as formed by the β-galactosidase reaction with the above-mentioned substrate by means of colorimetry, photo-absorptiometry, fluorophotometry, redox measurement, high-performance liquid chromatography, etc. It is also possible that the enzymatic reaction is conjugated with galactose dehydrogenase or the like and the amount of the coenzyme of reduced type as formed is quantitatively determined.

The determination method of the present invention is described below.

A chelating agent and a sample are added to a buffer (50 to 1000 mM solution) preferably as adjusted at pH of from 5.0 to 10.0. A substrate for β-galactosidase and β-galactosidase are added to the reaction liquid, where β-galactosidase reaction is conducted. Any desired means may be employed to add the substrate for β-galactosidase and β-galactosidase. For example, if the substrate (250 μM to 60 mM) for β-galactosidase is first added, β-galactosidase (35 U/liter to 30 KU/liter) is added later or. If β-galactosidase (250 U/liter to 60 KU/liter) is first added, the substrate (250 μM to 60 mM) for β-galactosidase is added later on. The β-galactosidase reaction is conducted at from 8° to 50° C. The amount of the substrate for β-galactosidase that has decreased in the reaction liquid is measured according to any of the above-mentioned methods, or the amount of the β-galactosidase reaction product that has increased in the reaction system is measured according to any of the above-mentioned methods and the amount of the substrate that has been consumed by the β-galactosidase reaction is determined. In the present enzymatic reaction, since the amount of the substrate as consumed by the reaction corresponds to the amount of sodium in the sample, it is possible to quantitatively determine the amount of sodium in the sample by means of the present measuring method.

In carrying out the method of the present invention, surfactants such as Triton X-100, etc. may be added to the reaction liquid, if desired, in order to prevent the reaction liquid from becoming cloudy. Also if desired, it is possible to add proteins such as bovine serum albumin (BSA), human serum albumin (HSA), human immunoglobulin, egg white albumin, etc., solubilizers such as dimethylsulfoxide, etc., antioxidants such as dithiothreitol, etc., activators such as magnesium sulfate, etc.

BEST MODES FOR CARRYING OUT THE INVENTION

Figure 1:
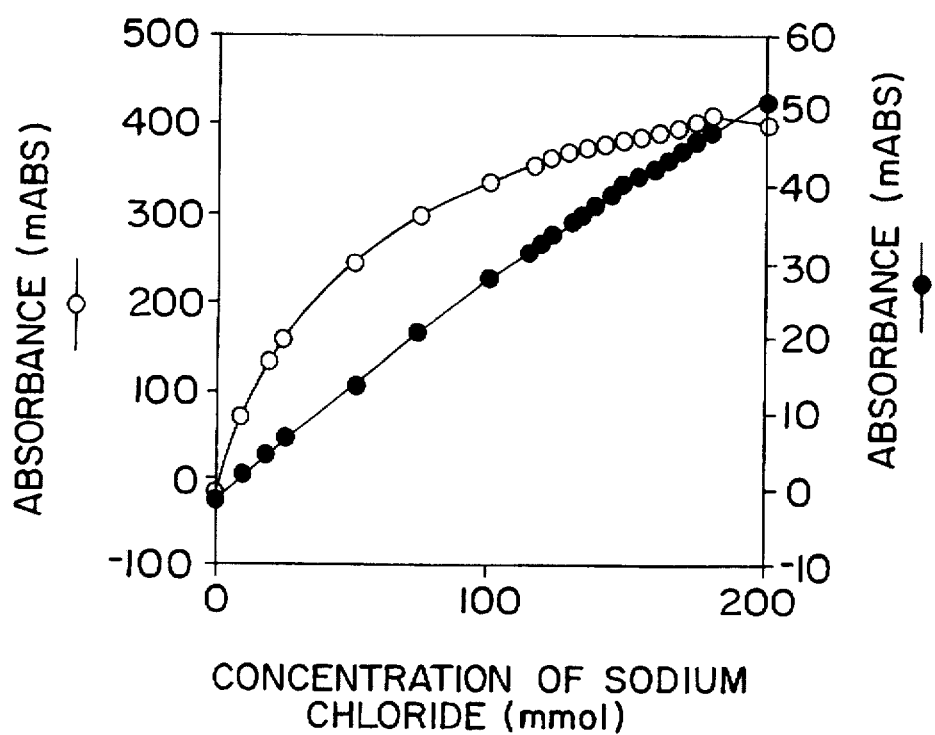
FIG. 1 shows the calibration curves of sodium ions, in which the line represented by (-●-) was obtained in the presence of EDTA and the line represented by (-○-) was obtained in the absence of EDTA.

Examples of the present invention are mentioned below, which, however, are not intended to restrict the scope of the invention.

Example 1

(1) Preparation of standard liquids for sodium calibration curve:

Sodium chloride (produced by Wako Pure Chemicals Co.) was diluted with distilled water to obtain standard liquids having a sodium chloride concentration of 0, 10, 20, 25, 50, 75, 100, 115, 120, 125, 130, 135, 140, 145, 150, 155, 160, 165, 170, 175, 180 and 200 mM, wish which a sodium calibration curve is obtained hereunder.

(2) Quantitative determination of sodium:

One of the standard liquids for obtaining a sodium calibration curve or a serum sample (4 μl in each one measurement) was put into a sample cup, and a first reagent (300 μl in each one measurement) comprised of 5 mM of DL-dithiothreitol (produced by Sigma Co.), 11 mM of magnesium sulfate (produced by Panto Chemical Co.), 4000 U/liter of β-galactosidase (produced by Sigma Co.) and 440 of trishydrochloride buffer (pH 7.75) containing 30.7 mM of EDTA·4H (produced by Dojin Chemical Co.) was added thereto and reacted at 37° C. for 5 minutes. Next, a second reagent 100 μl in each one measurement) comprising 15 mM of 2-nitrophenyl-β-D-galactopyranoside (produced by Tokyo Chemical Co.) in distilled water was added thereto and reacted at 37° C. The amount of p-nitrophenyl as formed within one minute was obtained by measuring the visible-ray absorbance at 405 nm, using Hitachi 7250 Model Analyzer. The calibration curve thus obtained is shown in FIG. 1.

According to the known method using Cryptofix, a calibration curve which is linear only within the range of the sodium ion concentration of from 110 to 160 mM is obtained (see Clinical Chemistry, Vol. 34, p. 2295, 1988). However, according to the method of the present invention using EDTA, a calibration curve which is linear throughout the whole range of the sodium ion concentration of 200 mM or less was obtained, as shown in FIG. 1.

Example 2

(2) Determination of sodium ions using EDTA:

A sodium ion calibration curve was obtained in the same manner as in Example 1, except that EDTA with varying concentrations 10, 20, 25, 50, 100, 200, 300, 400, 410 and 450 mM was used. The correlation coefficient was obtained via the regression on equation for the linear function of the calibration curve thus obtained and shown in Table 1.

TABLE 1

| Concentration of EDTA (mM) | Correlation Coefficient |
| --- | --- |
| 0 | 0.869 |
| 10 | 0.873 |
| 20 | 0.897 |
| 25 | 0.968 |
| 50 | 0.983 |
| 100 | 0.999 |
| 200 | 0.999 |
| 300 | 0.988 |
| 400 | 0.965 |
| 410 | 0.896 |
| 450 | 0.888 |

Table 1 indicates that the correlation coefficient is more than 0.95 when from 25 to 400 mM of EDTA was used and that reliable data are obtained by the measurement using EDTA.

Example 3

(3) Quantitative determination of sodium ions using CyDTA:

In the same manner as in Example 2 except that CyDTA with varying concentrations, 1, 2, 10, 50, 100, 200, 300, 400, 410 and 450 mM was used, the correlation coefficient was obtained via the regression equation for the linear function of the sodium ion calibration curve and shown in Table 2.

TABLE 2

| Concentration of CyDTA (mM) | Correlation Coefficient |
|---|---|
| 0 | 0.869 |
| 1 | 0.888 |
| 2 | 0.976 |
| 10 | 0.989 |
| 50 | 0.988 |
| 100 | 0.986 |
| 200 | 0.980 |
| 300 | 0.978 |
| 400 | 0.964 |
| 410 | 0.894 |
| 450 | 0.885 | table 2 indicates that the correlation coefficient is more than 0.95 when from 2 to 400 mM of CyDTA was used and that reliable data are obtained by the measurement using CyDTA.

Example 4

(4) Quantitative determination of sodium ions TTHA:

In the same manner as in Example 2 except that TTHA with varying concentrations, 0, 20, 25, 50, 100, 200, 300, 400, 410 and 450 mM was used, the correlation coefficient was obtained via the regression equation for the linear function of the sodium ion calibration curve and shown in Table 3.

TABLE 3

| Concentration of TTHA (mM) | Correlation Coefficient |
|---|---|
| 0 | 0.869 |
| 10 | 0.892 |
| 20 | 0.945 |
| 25 | 0.988 |
| 50 | 0.995 |
| 100 | 0.997 |
| 200 | 0.995 |
| 300 | 0.985 |
| 400 | 0.953 |
| 410 | 0.905 |
| 450 | 0.884 |

Table 3 indicates that the correlation coefficient is more than 0.95 when from 25 to 400 mM of TTHA was used and that reliable data are obtained by the measurement using TTHA.

Example 5

In the same manner as in Example 2 except that 30 mM of DTPA, DPTA-OH, EDDP, EDTPO, IDA, HIDA, NTDA, or EGTA (as a control) was used, the correlation coefficient for each chelating agent was obtained via the regression equation for the linear function of the sodium ion calibration curve. The data are shown in Table 4.

TABLE 4

| Cleating Agent | Correlation Coefficient |
|---|---|
| Control | 0.869 |
| EGTA | 0.884 |
| DTPA | 0.989 |
| DPTA-OH | 0.925 |
| EDDP | 0.914 |
| EDTPO | 0.925 |
| IDA | 0.878 |
| HIDA | 0.890 |
| NTP | 0.898 |

From Table 4, it is known that the correlation coefficient of the sodium ion calibration curve with each of the above-mentioned chelating agents is higher than that with the control but only DTPA gave the correlation coefficient of higher than 0.95.

INDUSTRIAL APPLICATION

The present invention relates to a method of quantitative determination of sodium ions using β-galactosidase reaction in the presence of a chelating agent.

We claim:

1. A method of quantitative determination of sodium ions in a sample using β-galactosidase, wherein the β-galactosidase is reacted in the presence of at least one chelating agent comprising 2 to 400 mM of 1,2-cyclohexanediamine-N,N,N',N'-tetraacetic acid, 25 to 400 mM of ethylenediamine-tetraacetic acid, 25 to 400 mM of triethylenetetramine-hexaacetic acid, or 10 to 400 mM of diethylenetriamine-N,N,N',N",N"-pentaacetic acid.

2. The method as claimed in claim 1, wherein the chelating agent is from 2 to 400 mM of 1, 2-cyclohexanediamine-N,N,N',N'-tetraacetic acid.

3. The method as claimed in claim 1, wherein the chelating agent is from 25 to 400 mM of ethylenediamines-tetraacetic acid.

4. The method as claimed in claim 1, wherein the chelating agent is from 25 to 400 mM of triethylenetetramine-hexaacetic acid.

* * * * *

UNITED STATES PATENT AND TRADEMARK OFFICE
CERTIFICATE OF CORRECTION

PATENT NO. : 5,766,870

DATED : June 16, 1998

INVENTOR(S): KAYOKO SHIGENOBU ET AL.

It is certified that error appears in the above-identified patent and that said Letters Patent is hereby corrected as shown below:

Title page, item

[57] ABSTRACT

Line 5, "of" should be deleted.
Line 7, "triethylenetetranine-hexaacetic" should read --triethylenetetramine-hexaacetic--.
Line 8, "1,3 -diminopropan-2-ol-N,N'," should read --1,3 -diminopropan-2-ol-N,N,N',--.
Line 11, "iminodiacetic" should read --imino-diacetic--.
Line 12, "nitrilotriacetic" should read --nitrilo-triacetic--.
Line 12-13, Close up paragraphs.

COLUMN 1

Line 16, "sample" should read --sample,--.

COLUMN 2

Line 8, "-penteacetic" should read ---pentracetic--.
Line 42, "Good" should read --GOOD--.
Line 44, "[Ec. 3.2.1.233]" should read --[EC 3.2.1.23]--.

COLUMN 3

Line 5, "fluorophotornetry," should read --fluoro-photometry--.
Line 66, "wish" should read --with--.

UNITED STATES PATENT AND TRADEMARK OFFICE
CERTIFICATE OF CORRECTION

PATENT NO. : 5,766,870

DATED : June 16, 1998

INVENTOR(S) : KAYOKO SHIGENOBU ET AL.

It is certified that error appears in the above-identified patent and that said Letters Patent is hereby corrected as shown below:

COLUMN 4

Line 7, "Panto" should read --Kanto--.
    Line 9, "trishydrochloride" should read
      --tris-hydrochloride--.
    Line 12, "100 µl" should read --(100 µl--.
    Line 32, "Determination" should read --Quantitative
      determination--.
    Line 37, "on" should be deleted.

COLUMN 5

Line 15, "table 2" should read --Table 2--.
    Line 21, "TTHA:" should read --using TTHA:--.
    Line 23, "0, 20," should read --0, 10, 20,--.
    Line 50, "NTDA," should read --NTP--.

UNITED STATES PATENT AND TRADEMARK OFFICE
CERTIFICATE OF CORRECTION

PATENT NO. : 5,766,870

DATED : June 16, 1998

INVENTOR(S) : KAYOKO SHIGENOBU ET AL.

It is certified that error appears in the above-identified patent and that said Letters Patent is hereby corrected as shown below:

<u>COLUMN 6</u>

```
Line 44, "ethylenediamines-" should read
    --ethylenediamine---.
```

Signed and Sealed this

Twenty-first Day of September, 1999

Attest:

Q. TODD DICKINSON

*Attesting Officer*  *Acting Commissioner of Patents and Trademarks*